United States Patent
Orthoefer (12) 
(10) Patent No.: US 6,312,703 B1
(45) Date of Patent: Nov. 6, 2001

(54) COMPRESSED LECITHIN PREPARATIONS

(75) Inventor: Frank T. Orthoefer, Chesterfield, MO (US)

(73) Assignee: Lecigel, LLC, Winchester, VA (US)

( * ) Notice: Subject to any disclaimer, the term of this patent is extended or adjusted under 35 U.S.C. 154(b) by 0 days.

(21) Appl. No.: 09/245,289

(22) Filed: Feb. 5, 1999

Related U.S. Application Data (60) Provisional application No. 60/073,990, filed on Feb. 6, 1998.

(51) Int. Cl.[7] ............... A61K 9/00; A61K 9/127; A61K 31/685
(52) U.S. Cl. ............ 424/401; 424/400; 424/450; 424/59; 424/65; 514/78; 514/844
(58) Field of Search ............... 424/400, 450, 424/401, 59, 65; 514/78, 844–848

(56) References Cited

U.S. PATENT DOCUMENTS

| | | |
|---|---|---|
| 4,221,784 | 9/1980 | Growdon et al. |
| 4,374,082 | 2/1983 | Hochschild . |
| 4,684,520 | 8/1987 | Bertelli . |
| 4,762,658 | 8/1988 | Rothfuss et al. |
| 4,780,456 | 10/1988 | Pistolesi . |

(List continued on next page.)

FOREIGN PATENT DOCUMENTS 0 354 442 * 2/1990 (EP) .

OTHER PUBLICATIONS

Orthoefer, F., *Lecithin and Health*, Vital Health Pub., Bloomingdale, IL, p. 21.

Wilson, T. et al, Soy Lecithin Reduces Plasma Lipoprotein Cholesterol and Early Atherogenesis in Hypercholesterolemic Monkeys and Hamsters: Beyong Linoleate. *Atherosclerosis* (1998); 140:147–153.

Wojcicki, J. et al, Clinical Evaluation of Lecithin as a Lipid–lowering Agent.

Hunt, C. et al, Hyperlipoproteinaemia and Atherosclerosis in Rabbits Fed Low–level Cholesterol and Lecithin; *British J. of Experimental Pathology* (1985) 66, 35–46.

FASEB, Effects of Consumption of Choline and Lecithin on Neurological and Cardiovascular Systems, (1981, August).

Kato, A. et al, Effect of Egg Yolk Lecithin on Transdermal Delivery of Bunazosin Hydrochloride, *J of Pharmacy and Pharmacology* (May, 1987); 39(5): 399–400 (Abstract only).

Willimann, H. et al, Lecithin Organogel as Matrix for Transdermal Transport of Drugs, *J of Pharmaceutical Sciences*, (Sep. 1992; 81(9): 871–874 (Abstract only).

(List continued on next page.)

*Primary Examiner*—Gollawudi S. Kishore
(74) *Attorney, Agent, or Firm*—Hunton & Williams

(57) ABSTRACT

The present invention relates to compositions primarily comprised of phospholipids, commercially known as lecithin, wherein the phospholipids form a solid mass—a liquid crystal phospholipid (LCP)—without the use of emulsifiers or other ingredients which are typically used as carriers for phospholipids. The invention also relates to the methods for making the phospholipid compositions. More particularly, the invention relates to a physical form of phospholipids and its use as a topical cosmetic skin bar, as a nutrient supplement or as a pharmaceutical dosage form if taken orally. Regardless of the exact shape of the new phospholipid composition, it comprises an amount of phospholipid equal to at least about 20% by weight of the total product. The new composition of the phospholipids appears as a solid which is produced by subjecting granular or powdered phospholipids to high levels of pressure which result in the formation of the solid phospholipid composition.

16 Claims, 2 Drawing Sheets

U.S. PATENT DOCUMENTS

| | | |
|---|---|---|
| 4,783,450 | 11/1988 | Fawzi et al. . |
| 5,030,452 | 7/1991 | Curatolo . |
| 5,043,323 | 8/1991 | Bombardelli et al. . |
| 5,108,756 | 4/1992 | Curatolo . |
| 5,364,886 | 11/1994 | Loliger et al. . |
| 5,498,607 | 3/1996 | Hsia et al. . |
| 5,855,786 * | 1/1999 | Eggert ................................ 210/634 |
| 5,932,562 | 8/1999 | Ostlund, Jr. . |

OTHER PUBLICATIONS

Tesoriere, L. et al, Synergistic Interactions between Vitamin A and Vitamin E against Lipid Peroxidation in Phosphatidylchloline Liposomes; Archives of Biochemistry and Biophysics (Feb. 1, 1996); 326(1): 57–63.

Storozhok, N. et al, Effects of Synergism During Combined Antioxidant Action of Phosphatidylcholine with Natural and Synthetic Quinones; Vopr. Med. Khim. (Jan. 1994); 40(1):10–14 (Abstract only).

Hollander, D. et al, Effect of PLant Sterols, Fatty Acids and Lecithin on Cholesterol Absorption in vivo in the Rat; *Lipids*; vol. 15(6):395–400.

Levy, R. et al, A Quarter Century of Drug Treatment of Dyslipoproteinemia, with a Focus on the New HMG–CoA Reductase Inhibitor Fluvastatin, *Circulation* (Apr, 1993); 87(4 Suppl):III45–III53 (Abstract only).

Gurevich, V. et al, Polyunsaturated Phospholipids Increase the Hypolipidemic Effect of Lovastatin; *European J of Internal Medicine* (1997); 8:13–18.

Kidd, P. et al, Phospholipids as Membrane Foods: The Healthy Story of Lecithin and Phospholipids, Lucas Meyer GmbH, Pub. #18.

Williams, W.P. et al, The Pro–Liposome Method: A Practical Approach to the Problem of the Preparation and Utilization of Liposomes Suitable for Topical Applications; *Phospholipids; Characterization, Metabolism, and Novel Biological Applications*, Chapter 17, AOCS Press.

Payne, N. et al, Characterization of Proliposomes, *J of Pharmaceutical Sciences* (Apr. 1986); 75(4): 330–333.

Deo, M. et al, Proliposome–based Transdermal Delivery of Levonorgestrel, *J of Biomater Appl.* (Jul. 1997); 12(1):77–78 (Abstract Only).

Perrett, S. et al, A Simple Method for the Preparation of Liposomes for Pharmaceutical Applications: Characterization of the Liposomes; *J of Pharmacy of Pharmacology*, (Mar. 1991); 43(3):154–161 (Abstract only).

Turnaek, J. et al, Linkup of a Fast Protein Liquid Chromatography System with a Stirred Thermostated Cell for Sterile Preparation of Liposomes by Proliposome–Liposome Method . . . ; *Analytical Biochemistry* (Jul. 1997); 249(2):131–139.

Kirby, C. et al, A Simple Procedure for Preparing Liposomes Capable of High Encapsulation Efficiency Under Mild Conditions; *Liposome Technology*, vol. 1, Chapter 2, pp. 19–27.

Amselem, S. et al, Emulsomes, A New Type of Lipid Assembly.

Payne, N. et al, Proliposomes: A Novel Solution to an Old Problem; *J. of Pharmaceutical Sciences* (Apr. 1986); 75(4):325–329.

Perrett, S. et al, A Simple Method for the Preparation of Liposomes for Pharmaceutical Applications: Characterization of Liposomes; *J of Pharmacy and Pharmacology* (1991); 43:154–161.

Chandran, S. et al, Recent Trends in Drug Delivery Systems: Liposomal Drug Delivery System—Preparation and Characterization; *Indian J of Experimental Biology*, (Aug. 1997) 35:801–809.

* cited by examiner

COMPRESSED LECITHIN PREPARATIONS

This application claims priority to U.S. Provisional Application No. 60/073,990, filed Feb. 6, 1998.

FIELD OF THE INVENTION

The present invention relates to a solid composition comprised primarily of phospholipids (also known as lecithin), or enriched phospholipids, in an amount of at least about 20% up to 100%, and preferably 30% up to 100%, by weight of the total phospholipid composition. The composition of the present invention is in a surprising new form, which is referred to as liquid crystal phospholipid (LCP). The present invention also relates to the method of making the LCP. The solid phospholipid composition can be used as a cosmetic bar or can be used as a tablet to be taken orally or as a combination (in tablet or capsule form) to promote delayed release or rapid dispersibility.

BACKGROUND OF THE INVENTION

The term "phospholipid," also known as lecithin, as used herein does not refer only to a single phospholipid, such as phosphatidylcholine, but rather may comprise de-oiled granules or powder having approximately the following typical composition (Orthoefer, F., *Lecithin and Health*, Vital Health Pub, Bloomingdale, IL, p. 21.):

| | |
|---|---|
| Phosphatidylcholine | 23% |
| Phosphatidylethanolamine | 21% |
| Phosphatidylinositol | 19% |
| Phosphatidic Acid | 6% |
| Glycolipids | 14% |
| Other phospholipids | 15% |

In addition, the term "phospholipid" or lecithin also comprises any enriched phospholipid compound in which the phosphatidylcholine content exceeds 23%, the phosphatidylinositol content exceeds 19%, or the phosphatidylethanolamine exceeds 21%.

It has been known to use lecithin as an ingredient or a constituent in formulations for soaps, creams, and lotions, as well as other emulsions applied to the skin. These various emulsions containing lecithin have been used to moisturize skin and as medicated ointments for general applications, with the various emulsions and ointments rubbed onto the user's skin. In these formulations, lecithin serves the following purposes: 1) it is an emulsifier to promote solubilization of non-aqueous soluble components or medications into the aqueous phase, 2) it contributes to the stability of the emulsion, 3) it is an excellent moisturizer, 4) it delivers highly beneficial phospholipids to the skin, and 5) it contains vitamin E and polyunsaturated fats, both of which impart health benefits to the user's skin. While such emulsions and creams are useful in reducing dry skin, they are difficult to apply and leave a greasy or sticky feeling on the user's skin. The non-aqueous portions of the known emulsions are often simply oils which do not replenish moisture or oils lost from the skin. Thus, it would be desirable to have an ointment, treatment, or emulsion, which is easy to apply and does not leave a sticky or greasy feeling on a user's skin, but which is useful in moisturizing the skin, maintaining softness, and preventing loss of water and natural oils.

Lecithin is derived from soybeans and can be produced in liquid, powdered or granular form. While lecithin has been used in emulsions, products based only on phospholipids are few. U.S. Pat. No. 5,498,607 to Hsia et al. describes use of a topically applied phosphatidylcholine fraction of lecithin to reduce cholesterol. U.S. Pat. No. 4,221,784 to Grower et al. describes the oral administration of lecithin alone to restore memory loss. Administered in conjunction with the American Heart Association Step I diet, lecithin enhances the reduction of plasma cholesterol and LDL. In addition, lecithin is effective in reducing total cholesterol and triglycerides in hypercholesterolemic hamsters (Wilson, T., et al., "Soy Lecithin Reduces Plasma Lipoprotein Cholesterol and Early Atherogenisis in Hypercholesterolemic Monkeys and Hamsters: Beyond Linoleate", *Atherosclerosis* (1998) 140:147–153).

The positive effects of lecithin in reducing arterial plaque, besides decreasing LDL cholesterol, and increasing HDL cholesterol, are well known (Wojcicki, J. et al., "Clinical Evaluation of Lecithin as a Lipid-lowering Agent"; Hunt, C. et al., "Hyperlipoproteinaemia and Atherosclerosis in Rabbits Fed Low-level Cholesterol and Lecithin", *British J. of Experimental Pathology* (1985) 66: 35–46; FASEB, "Effects of Consumption of Choline and Lecithin on Neurological and Cardiovascular Systems" (1981, August).

U.S. Pat. No. 4,783,450 to Fawzi et al. describes the use of lecithin as a skin penetration enhancer designed for transdermal applications, in which the described skin is mucosal and bronchial. Kato ("Effect of Egg Yolk Lecithin on Transdermal Delivery of Bunazosin Hydrochloride", *J. of Pharmacy and Pharmacology*" (1987 May) 39(5): 399–400) and Willimann ("Lecithin Organogel as Matrix for Transdermal Transport of Drugs", *J. of Pharmaceutical Sciences* (1992 September) 81(9): 871–874) report on the effectiveness of egg lecithin and lecithin gels as efficient carriers of drugs through the skin.

Among the reasons skin products have not been based on pure phospholipids are that granular and powdered lecithin are not easily applied to the skin, while liquid lecithin, even diluted to 50%, is viscous and not easily spreadable. Because of the unique benefits derived from using pure phospholipid, it would be especially desirable to have a phospholipid composition which is a purified form with the consistency of a cosmetic bar of soap, so that the phospholipid could be applied easily to a user's skin. Further, it would be desirable to have the solid phospholipid bar incorporate dermatological preparations which would be beneficial and advantageous for the treatment of skin ailments and diseases.

In addition, preparations of a solid phospholipid length would be desirable for the oral administration of an almost pure phospholipid nutrient supplement. Meck et al. ("Characterization of the Facilitative Effects of Perinatal Choline Supplementation on Timing and Temporal Memory", *Neuroreport* (Sep. 8, 1997) 8(13):2831–2835 and (Sep. 29, 1997) 8(14):3045–3059) showed that perinatal choline supplementation has long-term effects on working and reference memory components in rats. Pyapali, G. K. et al., "Prenatal Dietary Choline Supplementation Decreases the Threshold for Induction of Long-Term Potentiation in Young Adult Rats", *J. of Neurophysiology* (April 1998) 79(4):1790–1796, found that the induction of Long-Term Potentiation was enhanced in adult rats that had received prenatal choline supplementation. Oral lecithin supplements currently are prepared based on either liquid or granular lecithin products. The liquid lecithin products are encapsulated with gelatin and provide an easily consumed product. However, these liquid lecithin products have decreased potency. Formulated liquid lecithin supplements consists most generally of water with a phospholipid content of less than 10%. These lecithin compositions suffer from being microbiologically unstable and require further processing to render them shelf-stable.

Oral supplements based on the higher potency granular lecithin are consumed as powders or granules by mixing with other foods such as ready-to-eat cereals or dissolved in drinks such as fruit juice. These products are difficult to dissolve and generally have an undesirable texture and taste. Formulated dry lecithin supplements for use in milk or juice solids are intended for hydration prior to consumption. These, however, suffer from low potency and high cost.

Thus, it is desirable to have a solid phospholipid composition comprised primarily of phospholipids which: 1) can be used externally to moisturize and protect skin, 2) can be used externally in a mixture with phytochemicals and medicaments for the treatment of skin ailments and, 3) can be formulated into a pill or tablet and taken orally as a nutritional supplement.

Preparations of a solid phospholipid bar also would be desirable for the oral administration of nutraceutical and pharmaceutical drugs. The use of Coenzyme Q10 and lecithin taken orally is given in U.S. Pat. No. 4,684,520 to Bertelli, which describes the combination restoring cerebral function and inhibiting the formation of atherosclerotic lesions. U.S. Pat. No. 4,780,456 to Pistolesi describes a dietetic composition for the treatment of atherosclerotic pathologies which treatment incorporates lecithin and eicosapentaenoic oils. U.S. Pat. No. 5,043,323 to Bombardelli et al. states that the oral consumption of lecithin with plant flavonoids is an effective treatment for inflammation, altered platelet aggregation and other diseases. These referenced compounds may be ingested as capsules, tablets, granules, gels or syrups. However, the beneficial effects of phospholipid are minimal in these products either because the ratio of drugs to phospholipid is too high, or because individual fractions of soy phospholipids are used to produce the compound. Therefore, it is desirable to have a solid composition comprised primarily of phospholipids which, in addition to the uses given above, can be formulated into a pill or tablet that contains drugs and nutritional compositions as additives, which pills and tablets can be taken orally.

Also it would be desirable to have a preparation of solid phospholipid composition in which the dispersibility or release may be controlled through use of modified, high potency lecithin-creating a compound to enhance or delay release of active ingredients.

SUMMARY OF THE INVENTION

The present invention is directed to a composition comprised of an amount of phospholipid or enriched phospholipid equal to at least about 20% by weight of the total composition and can contain an amount of phospholipid equal to as much as 100% by weight of the total composition. The solid phospholipid composition of the invention is a very high viscosity liquid or liquid crystal which has a homogeneous and continuous structure. The present invention also relates to the method of forming the phospholipid composition. The phospholipid composition is formed by compressing and extruding an amount of phospholipid equal to at least about 20% by weight of the total composition under an amount of pressure equal to at least about 100 pounds per square inch (psig).

The phospholipid composition is advantageous because it can form a cosmetic bar which takes advantage of the monomolecular film-forming properties of phospholipid and imparts numerous health benefits to the skin of the user. While additives may be included, phospholipids without any additives have desirable cosmetic properties. Not only do phospholipids have health benefits, but they can also serve as a carrier for dermatological preparations desirable for skin health. The bar may contain substances such as waxes, fatty acids, vitamins, ultraviolet light blockers, germicides, phytochemicals, oils and additional compounds. Thus, the present invention relates to a solid liquid crystal phospholipid composition which may contain additives for use on human skin and a method for making the solid liquid crystal phospholipid (LCP) composition.

In addition, the LCP composition can be compressed into a tablet in a size suitable for ingestion so as to prepare a high potency oral phospholipid tablet. When taken orally without other ingredients, phospholipids impart many benefits to the consumer including, among others: they act as antioxidants, are a natural source of choline, reduce platelet aggregation, improve elasticity of blood vessels, dissolve gall stones, aid in memory retention, enhance physical endurance, and detoxify the liver. This latter characteristic of the choline-containing phospholipid would be advantageous for use after administration of certain pharmaceuticals such as anesthetics (Halothane) which are known to compromise liver function. In addition to providing the aforementioned benefits, phospholipid tablets can be made to contain other desirable nutritional constituents, such as vitamins, chelated minerals, amino acids, marine and plant lipids, antioxidants (i.e., lipoic acid and coenzyme Q), proteolytic enzymes, terpenes (i.e., carotenoids, xanthophylls, limonoids, phytosterols, and herbal terpenes), phenols (i.e., flavones, flavonols, flavanones, anthocyanidins, catechins, isoflavones), thiols, glucosinolates, indoles, isoprenoids, among others. For example, lecithin is well known for its synergistic action with vitamin E, plant sterols and other lipid soluble nutrients (U.S. Pat. No. 5,364,886 to Loliger et al.; Tesoriere, L. et al., "Synergistic Interactions between Vitamin A and Vitamin E against Lipid Peroxidation in Phosphatidylcholine Liposomes", *Archives of Biochemistry and Biophysics* Feb. 1, 1996, 326(1): 57–63; Storozhok, N. et al., "Effects of Synergism During Combined Antioxidant Action of Phosphatidylcholine with Natural and Synthetic Quinones",. *Vopr. Med. Khim.* (1994 January 40(1):10–14; Hollander, D. et al., "Effect of Plant Sterols, Fatty Acids and Lecithin on Cholesterol Absorption in vivo in the Rat", *Lipids* 15(6):395–400). Therefore, it would be advantageous to incorporate such nutrients into the LCP which, when ingested, would deliver a synergistic combination of nutrients to the consumer.

The solid phospholipid tablet can also contain pharmaceutical constituents which are desirable for oral administration, such as antibiotics, cardiac drugs, sedatives, anti-convulsives, and analgesics (such as acetaminophen), among others. Alternatively, the LCP can be formed into a capsule that contains the pharmaceutical constituents.

The biochemical process which takes place during the mixing of the drug or nutrient and the extrusion of the solid phospholipid composition is called proliposome formation. Several examples of the proliposome-liposome formation are known (Williams, W. P. et al., "The Pro-Liposome Method: A Practical Approach to the Problem of the Preparation and Utilization of Liposomes Suitable for Topical Applications", in Phospholipids: *Characterization, Metabolism, and Novel Biological Applications*, Chapter 17, AOCS Press; Payne, N. et al., "Characterization of Proliposomes,". *J. Pharmaceutical Sciences* (1986 April) 75(4):330–333; Deo, M. et al., "Proliposome-based Transdermal Delivery of Levonorgestrel", *J. Biomater Appl.* (1997 July) 12(1):77–78; Perrett, S. et al., "A Simple Method for the Preparation of Liposomes for Pharmaceutical Applications: Characterization of the Liposomes", *J. Pharmacy and Pharmacology*, (1991 March) 43(3) :154–161; Turanek, J., et al., "Linkup of a Fast Protein Liquid Chromatography System with a Stirred Thermostated Cell for Sterile Preparation of Liposomes by Proliposome-Liposome Method", *Analytical Biochemistry* (1997 July) 249(2):131–139). In this process, the powdered or granular phospholipid is mixed with the nutrient or drug active ingredient in the presence of a small amount of water. According to the present invention, after compression and ingestion, the pro-liposomes become hydrated in the gut. The water in the gut combines with the active ingredients and said active ingredients are effectively trapped in the liposomes thus formed. A small amount of monoglyceride or other dispersant also may be added with the active ingredients to aid in the disintegration of the pro-liposome in the small intestine and to assure passage of the active ingredient containing liposomes into the thoracic lymph.

Thus, the present invention relates to a solid phospholipid composition which may contain active ingredients for oral ingestion in extruded tablet form, which tablets are pro-iposomes that are converted into liposomes when they are hydrated by water in the small intestine.

DETAILED DESCRIPTION OF THE PREFERRED EMBODIMENTS

The present invention relates to liquid crystal phospholipid (LCP) compositions for use in cosmetics, dermatological medicaments, nutritional supplements and drug preparations wherein the bioavailability of the active ingredients may be controlled. This invention also relates to the method of making the LCP compositions.

The LCP compositions are made from powdered or granular phospholipids, either enhanced with phosphatides or not, having a phospholipid composition as expressed as an acetone insoluble index equal to or greater than 90%. Surprisingly, when subjected to pressure, the powdered or granular phospholipids are compressed and extruded into a new form, referred to as liquid crystal phospholipid, which is essentially a change of state of the phospholipid to a previously unknown form that has novel and useful properties. In this solid composition, the phospholipid molecules bind to one another to form a substantially homogeneous and continuous structure. In essence, the phospholipid molecules bind to one another similar to a meltable wax composition. The phospholipid is not, however, a meltable composition, but degrades or decomposes upon heating. Also, the phospholipid molecules bind to one another to form a solid matrix which can be used as a carrier for nutrients, minerals, phytochemicals, and drugs or which can be used alone as a LCP composition.

Phospholipids have a number of desirable health benefits and are used in a number of food and cosmetic products for a variety of different uses. Phospholipid compounds are high in vitamin E and fatty acids, which are beneficial to the general nutrition of animals and which are also beneficial when placed on the skin. Traditionally, phospholipids have been an additive used to help emulsify food products, as well as being placed in cosmetics and other goods as an emulsifier. To date, a high percentage solid granular phospholipid extruded bar or tablet is yet to be commercially available. U.S. Pat. No. 4,762,658 to Rothfus (abandoned) describes using a rotary tablet press to form de-oiled lecithin. U.S. Pat. No. 4,374,082 to Hochschild (abandoned) describes a technique for extruding powdered lecithin into dosage forms. However, this process only uses 23% phospholipid in the mixture and makes no provision to subject the mixture to at least 100 psig for a sustained period of time and thus the LCP of the present invention did not result. The formation of the powdered or granular phospholipids or enriched phospholipids into a continuous network of phospholipid having a homogeneous appearance is partially dependent upon the moisture content of the phospholipids and the nature of the additives in the powdered phospholipids. The addition of oils such as jojoba, borage, black currant, evening primrose, tocopherol, tocotrienol, or vegetable oils, to as much as 25% by weight of the powdered or granular phospholipid, results in a mix that is easily compressed into a tablet or bar with a deformable solid structure and texture. The higher the oil content within the powdered or granular phospholipids or enriched phospholipids, the easier to compress the phospholipids into a solid matrix and the softer the final texture. The addition of phytochemicals such as boswellia serrata, ginkgo biloba, and silybin to as much as 20% by weight results in a somewhat harder and rougher textured extrusion. The addition of moisture to upwards of 10% also presents an easier to compress formulation and a smooth textured final structure. However, it is preferred to have a moisture content of less than about 5% in the powdered or granular phospholipids prior to compressing. The phospholipid granules are sensitive to extraneous moisture so that the relative humidity of the extrusion room should be maintained at approximately less than 25% to prevent over compaction and binding of the machine. The addition of plant sterols to as much as 33% facilitates the extrusion process since the sterols are hydrophilic. This characteristic likely allows the sterols to absorb residual moisture from the phospholipid prior to extrusion. This advantage is in addition to the use of plant sterols for health purposes.

Formation of the solid LCP composition is initiated by selecting an amount of the powdered or granular phospholipids which are commercially available and come in a variety of grades, including food grade, technical, bleached, unbleached, and enriched. Regardless of the type of powdered or granular phospholipids selected, it is preferred for convenience that the phospholipids have a phospholipid content of at least 90% but not limited to this amount and be oil free or de-oiled. Specific phospholipid components, which are available for use in the present invention, include, for example, Phosphatidylcholine, Phosphatidylethanolamine and Phosphatidylinositol. In addition, synthetic lecithins, such as YN100 Cadberry, a synthetic phosphated diglyceride, and other synthetic phospholipids may be used.

The formulas for the specific phospholipid components are as follows:

Phosphatidylethanolamine

Phosphatidylinositol

Phosphatidylcholine

The terms R and R' in the above disclosed phospholipid components are fatty acids having the formula $CH_3(CH_2)_n COOH$, with n equal to between 4 and 22. Additionally, lecithin has a general formula of $C_8H_{17}O_5NRR'$ where R and R' are fatty acids having the formula $CH_3(CH_2)_n COOH$, with n equal to between 4 and 22. One of skill in the art will appreciate that other fatty acids containing other R groups, including those with a cyclic structure and with or without heteroatoms, may also be used according o the present invention.

The powdered or granular phospholipid or enriched phospholipid components are used to form a LCP composition which can contain an amount of additive. The solid LCP composition is made by placing a desirable amount of the phospholipids in a means for compressing the powdered or granular phospholipid. The amount of the phospholipids added is equal to between about 20% and 100%, or preferably form 30% to 100% by weight of the LCP composition. The means can be such that a batch process is performed wherein at least one solid LCP bar is produced at a time or it can be a continuous process, involving for example an extruder, wherein the phospholipids can be compressed to continually form solid LCP extrusions. A twin screw extruder has been used to produce particularly useful LCP extrusions.

Regardless of whether a batch or continuous process is used, a device must be used which can hold an amount of the phospholipids and which can apply an amount of pressure to the phospholipids to form a solid composition. The amount of pressure applied to form the solid LCP bar is equal to at least 100 pounds per square inch gauge (psig) in a batch process and preferably is equal to about 1200 psig, although lighter pressures may be used to achieve the same result. Also, the means for forming the solid LCP composition in a batch process must be capable of retaining the phospholipids under pressure for at least 15 seconds and preferably for approximately 1 minute. As the pressure is increased the time necessary to form the LCP bar decreases. Regardless of the time or pressure, the powdered phospholipids must be compressed for a sufficient amount of time at a sufficient pressure in order to form a solid LCP composition having a density ranging between 0.95 and 1.2.

An amount of an additive can be placed in the pressure means with the powdered phospholipid, with the additive or additives added in an amount equal to between 0.01% by weight and about 80% by weight of the total solid LCP composition. A variety of additives can be mixed with the powdered phospholipid to form said LCP compositions, including fragrances, oils, moisturizers, vitamins, UV blockers, humectants, cleaning agents, colloidal meals, nutritional supplements, chelated minerals, herbal extracts, essential fatty acids, drugs, phytochemicals, amino acids, disintegrants and combinations thereof.

The solid phospholipid tablet can also contain pharmaceutical constituents which are desirable for oral administration, such as antibiotics, cardiac drugs, sedatives, anti-convulsives, and analgesics (such as acetaminophen), among others. One example is given here: HMG-CoA reductase inhibitors are prescribed for those persons who suffer from high plasma cholesterol levels and the consequential threat of cardiovascular disease. Nicolosi and Wilson (private communication) studied the effects of Fluvastatin and soy phospholipid on hamsters. The data suggests that combining soy phospholipid with statin therapy may reduce the doses of statin that are necessary for beneficial cholesterol-lowering and lipoprotein profiles. A clinical trial using 60 hypercholesterolemic patients showed synergism between phospholipids and Lovastatin. Forty (40) mg/day of Lovastatin alone was required to reduce the LDL cholesterol level of patients to a value of 130, whereas a combined therapy of 75% phosphatidylcholine derived from soy phospholipids and Lovastatin required only 20mg/day to achieve the same level of LDL (Gurevich, V. et al., "Polyunsaturated Phospholipids Increase the Hypolipidemic Effect of Lovastatin", *European J. of Internal Medicine* (1997) 8:13–18). One disadvantage of statin drugs, as well as those of other drug classes mentioned above, is that they are known to have a deleterious effect on the liver. Lecithin with high choline content is recognized as enhancing liver improvement by causing cell repair and regeneration (Kidd, P. et al., "Phospholipids as Membrane Foods: The Healthy Story of Lecithin and Phospholipids", Lucas Meyer Gmbh., Pub.#18).

A variety of dissolution additives can be incorporated into the LCP allowing it to be more or less rapidly disintegrated. These dissolution additives include, but are not limited to: Calcium Steraroyl-2-Lactylate, Sodium Stearoyl Lactylate, Ethoxylated Monoglyceride, Polysorbate 60, Dry Monoglyceride, Starch, and Sucrose, as well as modified forms of phospholipids such as Hydroxylated Lecithin, Enzyme-Modified Lecithin, and Calcium-Linked Lecithin. This control over the disintegration rate of the LCP allows active ingredients, such as nutraceuticals and pharmaceuticals, which are also incorporated into the LCP, to become more or less is quickly absorbed or bioavailable.

Additionally, a simple means exists for creating a new type of timed-release dosage form. First, combining a slow dissolution additive with the phospholipids and an active ingredient to produce a slow acting LCP and, second, combining a rapid dissolution additive with the phospholipids and the same active ingredient to produce a fast acting LCP. The slow and fast acting LCPs are then ground and re-extruded to produce a timed-release dosage form.

Which additives will be added to the solid LCP will depend upon the characteristics desired in the finished product. For example, a solid LCP composition designed specifically to improve cardiovascular function may contain tocotrienols, coenzyme Q10, bioflavonoids, natural chelating agents, potassium, tocopherol, selenium and statins in addition to the phospholipids in an amount equal to at least about 20% by weight of the total solid LCP composition. A solid LCP composition designed specifically to reduce high blood pressure may contain Omega-3 oils, coenzyme Q10, quercetin, pycnogenol, calcium, magnesium and potassium in addition to the phospholipids in an amount equal to at least about 20% by weight of the solid LCP composition. In general, if the solid LCP is used as a carrier for a pharmaceutical, vitamin or nutritional supplement, the additives will be different than if the LCP is a carrier for a cosmetic composition.

The solid LCP composition can be formed into a variety of sizes and shapes. At the very least the solid LCP can be formed into a tablet which is 0.25 inch in diameter. The phospholipid composition can be compressed or extruded into a solid form using a die ranging between about 0.25 and about 1.25 inches in diameter. The thickness is variable upwards from about 0.4 inches, to about 6 inches.

The following are working examples demonstrating the production and use of solid LCP compositions. It will be appreciated by one of skill in the art that the invention is not limited to the following examples.

EXAMPLE 1

A solid cosmetic bar composition was made from phospholipid, so that the method of the present invention converted the powdered or granular phospholipids into a solid phospholipid bar composition having a specific gravity of 1.2. The cosmetic bar composition was made by adding 40 grams of powdered lecithin obtained from Archer Daniels Midland Co., having an acetone insoluble index of 98, to a die mounted on a hydraulic press. The die was purchased from VWR Scientific Products Inc located in Dallas, Tex. under catalog number 53887-003. The die had an internal diameter of 2.25 inches and an outside diameter of 3.825 inches. The hydraulic press was model number 2086, made by Carver, Inc. of Dallas Tex.

After the 40 grams of powdered phospholipid was added to the die, the die was closed so that the powdered phospholipid could not escape the die. Once the die was closed, the hydraulic press was activated and 5000 psig was applied to the powdered phospholipid for 5 minutes. The pressure caused the phospholipid to form a translucent solid phospholipid bar, similar to a bar of soap, having a specific gravity of 1.2 g/ml. The cosmetic bar made of phospholipid was then removed from the die. The bar was intact, had a diameter of 2.25 inches and was 3/8 inch thick.

The cosmetic bar made from phospholipid had an amber appearance and was a semi-transparent solid having the consistency of a soap bar. The cosmetic bar from the phospholipid was then tested on a human subject who used the cosmetic bar in the shower after washing, but in the same manner as a bar soap. After applying the cosmetic bar, the subject rinsed and dried with a towel. The subject observed a coat over his entire body surface which made the skin smooth and gave it a soft feel. The subject further observed that the coating was present for eight (8) hours and up to 12 hours later after application of the cosmetic bar to the skin.

The subject further observed that, after use, the cosmetic bar did not readily degrade and that it kept its shape after use in the shower, lasting two weeks.

EXAMPLE 2

The same procedure was used as in Example 1 except that 45 grams of powdered phospholipid, equal to 90% by weight of the total composition, were added to the die chamber along with 5 grams of white petrolatum, equal to 10% by weight of the total composition. Compression was similar to Example 1. Upon examination of the finished product, a translucent LCP bar was formed which was usable in the shower similar to hand soap, except it was used after rinsing, and then it too was rinsed off. After use, a thin layer of phospholipid and white petrolatum were formed on the subject's skin. It was observed that the thin film layer was especially desirable because it persisted for up to eight hours and relieved dry skin and discomfort associated with pruritis.

EXAMPLE 3

The same procedure was used as in Example 1 except 45 grams of powdered phospholipid, equal to 90% by weight of the total composition, were added to the die chamber along with 5 grams of USP Aquaphor, equal to 10% by weight of the total composition. The phospholipid and Aquaphor were mixed in a standard food processor prior to placement in the die chamber.

The translucent LCP bar similar to the cosmetic bar of Example 1 was formed, so that the cosmetic bar containing USP Aquaphor had the consistency of a bar soap. Again the cosmetic bar of the present example was used in a manner similar to the cosmetic bar disclosed in Example 2. The cosmetic bar of the present Example resulted in a uniform film on the skin of the user that resulted in a slight, desirable sheen to the skin surface and which provided a protective layer.

EXAMPLE 4

The same procedure used in Example 1 was followed except 40 grams of powdered phospholipid, equal to 80% by weight of the total composition, were added to the die chamber along with 10 grams of colloidal oatmeal, equal to 20% by weight of the composition.

The resulting phospholipid and oatmeal cosmetic bar was opaque and had the consistency of a bar of soap. The phospholipid and oatmeal bar was used in a similar way as the cosmetic bar disclosed in Example 2. Use of the phospholipid and oatmeal bar resulted in the formation of a thin layer on the skin of the user. The phospholipid and oatmeal bar was particularly useful in relieving the discomfort of pruritis.

EXAMPLE 5

A cosmetic bar similar to the bar discussed in Example 1 was prepared, but in place of a portion of phospholipid, 5 grams of lanolin was mixed with 45 grams of powdered phospholipid in a food processor. The 50 gram mixture was compressed as in Example 1.

The phospholipid lanolin bar was easily used in the shower, bath or after hand washing, especially when compared to treatment with a product as unctuous as lanolin. The bars last approximately 14 days.

EXAMPLE 6

A cosmetic bar similar to the bar discussed in Example 1 was prepared but in place of a portion of the phospholipid, 32 grams of borage oil (Bioriginal Food and Science Corp), 0.8 grams of green tea extract (Anhui Tongling Co), and 1.6 grams of tocotrienol complex (Eastman Chemical Co), was mixed with 45.6 grams of powdered phospholipid in a food processor. The 80 gram mixture was compressed as in Example 1.

The resulting phospholipid bar was easily applied in the shower, bath and after hand washing. This phospholipid bar and the ingredients contained therein was used as a precautionary agent against exposure to ultraviolet B radiation. The skin was soft and moist after use and the bars lasted approximately 14 days.

EXAMPLE 7

A cosmetic bar similar to that of Example 1 was prepared, but in place of a portion of the phospholipid, 9.4 grams of evening primrose oil (Now Foods) and 2.6 grams of tocotrienol complex was mixed with 111 grams of powdered phospholipid in a food processor. The 123 gram mixture was compressed as in Example 1.

The liquid crystal evening primrose oil (EPO) bar was readily used in the shower or bath after washing and rinsing. The EPO bar was used in the treatment of plaque-type psoriasis and was effective in reducing the itching and scratching associated with that ailment. The bars lasted approximately 12 days.

EXAMPLE 8

The die in Example 1 was modified by drilling a ¼-inch hole in the center of the die to permit an exit of the compressed powdered phosphoipid in an extruded manner.

The powdered phospholipid, equilibrated to less than 5% moisture was placed in the die. The die was elevated in the press to permit exit of the compressed phospholipid, and pressure was applied to equal approximately 800–1000 psig. The compressed phospholipid exited the die in a continuous translucent rope of ¼-inch diameter. The rope was cut into lengths having a weight equal to 900 milligrams. The cut lengths were then placed in a rotating pan and powder coated. The finished LCP product is usable as a pure oral phosphoipid consumable nutritional supplement.

EXAMPLE 9

Oral LCP tablets similar to the tablets discussed in Example 8 were prepared, but in place of a portion of the phospholipid, 5.8 grams of 400 IU α-tocopherol (Sundown Vitamins) was mixed with 17.5 grams of Central Soya Centrolex D 6440 powdered phospholipid in a food processor. The phospholipid α-tocopherol preparation was compressed for one minute at 5000 psig before it was extruded. This 23.3-gram mixture exited the die in a continuous translucent rope of ¼ inch in diameter. The extrusion was cut into lengths having a weight equal to 1200 milligrams each. These tablets were taken orally as a vitamin E supplement.

EXAMPLE 10

LCP tablets similar to the tablets discussed in Example 8 were prepared but in place of a portion of phospholipid, 4.7 grams of borage oil, 3.8 grams of boswellia serrata (Natural Remedies 60% active) and 0.5 grams of tocotrienol complex was mixed with 15 grams of phospholipid. This 24-gram composition exited the die after compression in a continuous translucent rope of ¼ inch in diameter. The extrusion was cut into lengths having a weight of 600 milligrams each. These tablets were taken orally twice per day by human subjects with psoriasis. They subjects reported that the combination of active ingredients in these tablets had significant benefit in reducing the itching associated with the psoriasis. Additional batches of this combination were extruded so that the test could be continued for 4 weeks.

EXAMPLE 11

Oral LCP tablets similar to the tablets discussed in Example 8 were prepared, but in place of a portion of the phospholipid, 6 grams of evening primrose oil, 6 grams of boswellia serrata, 0.6 grams of tocotrienol complex, and 0.6 grams of monoglyceride (American Ingredients Co Alphadim 90NLK) was mixed with 46 grams of phospholipid in a food processor. This 60 gram composition was extruded at a pressure of 1500 psig and exited the die as a continuous smooth textured rope which was cut into dosage units of 630 milligrams each. The LCP tablets were taken orally twice a day to suppress the effects of psoriasis. After two weeks of treatment, the subject reported that the itching was gone and the redness associated with this disease was substantially reduced.

EXAMPLE 12

Oral LCP tablets similar to the tablets discussed in Example 8 were prepared, but in place of a portion of the phospholipid, 33% by weight of plant sterols were mixed with 67% powdered phospholipid in a commercial grade mixer. The phospholipid sterol preparation was extruded in an APV Baker model MPF 50 extruder at a pressure of 850 psig and exited the die as a continuous, smooth-feeling rope which was cut into dosage units of 400 milligrams each. These extruded tablets developed a hard texture upon cooling suitable for an orally administered dosage form. The products of this Example were consumed to reduce the cholesterol in the blood.

EXAMPLE 13

Oral LCP tablets similar to the tablets discussed in Example 8 were prepared. A set of four formulations were extruded separately and contained components shown in Table 1.

Figure 1:
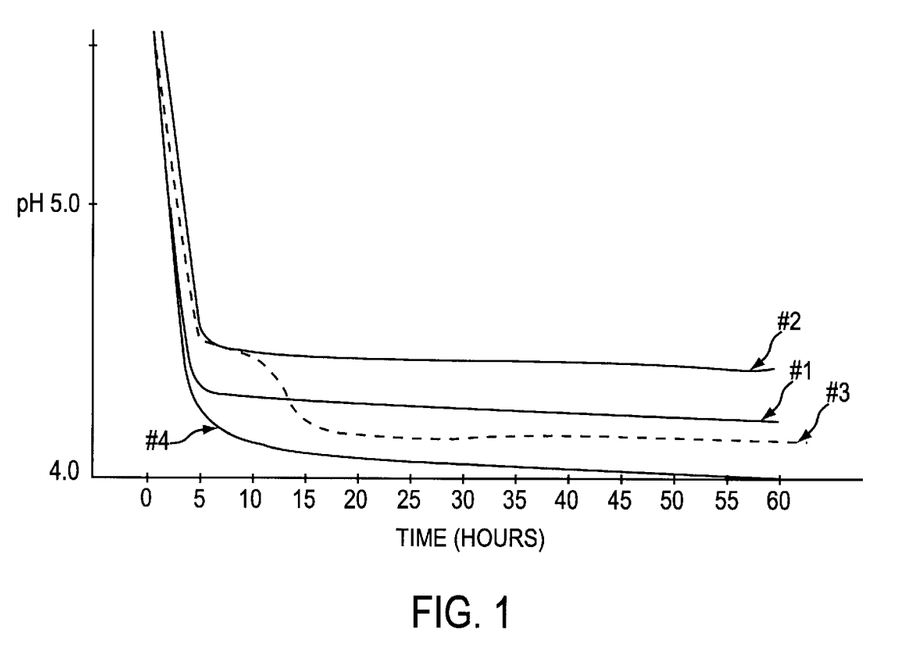
FIG. 1 is a depiction of the disintegration rate of LCP in water over time by measuring the change in pH. Four samples were tested, as described in example 13, containing phospholipids and Ca stearoyl-2 lactylate, ethoxylated monoglyceride, or confectioners sugar.

The phospholipid extrusions were cut into 600 mg pieces and placed in beakers with 150 ml of de-ionized water. Using an automatic stirrer, the water was stirred at about 100 rpm. As the LCP disintegrated, the pH of the solution was monitored with time. The pH data for each phospholipid sample is given in the following Table 2, and the disintegration curves are shown in FIG. 1.

TABLE 1

| Extrusion # | % Phospholipids | % Citric Acid | % Other Ingredients | Manufacturer of Other Ingredients |
|---|---|---|---|---|
| 1 | 95% | 5% | None | |
| 2 | 85% | 5% | 10% Ca Stearoyl-2-Lactylate | VERV Am Ingredients Company |
| 3 | 85% | 5% | 10% Ethoxylated Monoglyceride | EMG-20 Am Ingredients Company |

TABLE 1-continued

| Extrusion # | % Phospholipids | % Citric Acid | % Other Ingredients | Manufacturer of Other Ingredients |
|---|---|---|---|---|
| 4 | 85% | 5% | 10% Confectioners Sugar | Domino Sugar |

TABLE 2

| | Solution pH | | | |
|---|---|---|---|---|
| Time (min) | Sample #1 | Sample #2 | Sample #3 | Sample #4 |
| 0 | 6.28 | 6.28 | 6.28 | 6.28 |
| 5 | 4.34 | 4.51 | 4.50 | 4.24 |
| 10 | 4.29 | 4.46 | 4.45 | 4.12 |
| 15 | 4.28 | 4.44 | 4.20 | 4.09 |
| 20 | 4.27 | 4.43 | 4.17 | 4.07 |
| 30 | 4.26 | 4.425 | 4.16 | 4.05 |
| 40 | 4.24 | 4.42 | 4.15 | 4.03 |
| 50 | 4.23 | 4.41 | 4.14 | 4.02 |
| 60 | 4.20 | 4.40 | 4.13 | 4.00 |

The data shown in Table 2 and FIG. 1 indicate that the disintegration rate of the LCP, and hence the bioavailability of active ingredients, can be widely varied by incorporating such other ingredients into the LCP. The use of modified lecithins also changes the disintegration rate. Enzyme-modified phospholipids increase the speed of the LCP dissolution, while calcium-linked phospholipids decrease the rate of disintegration.

EXAMPLE 14

Figure 2:
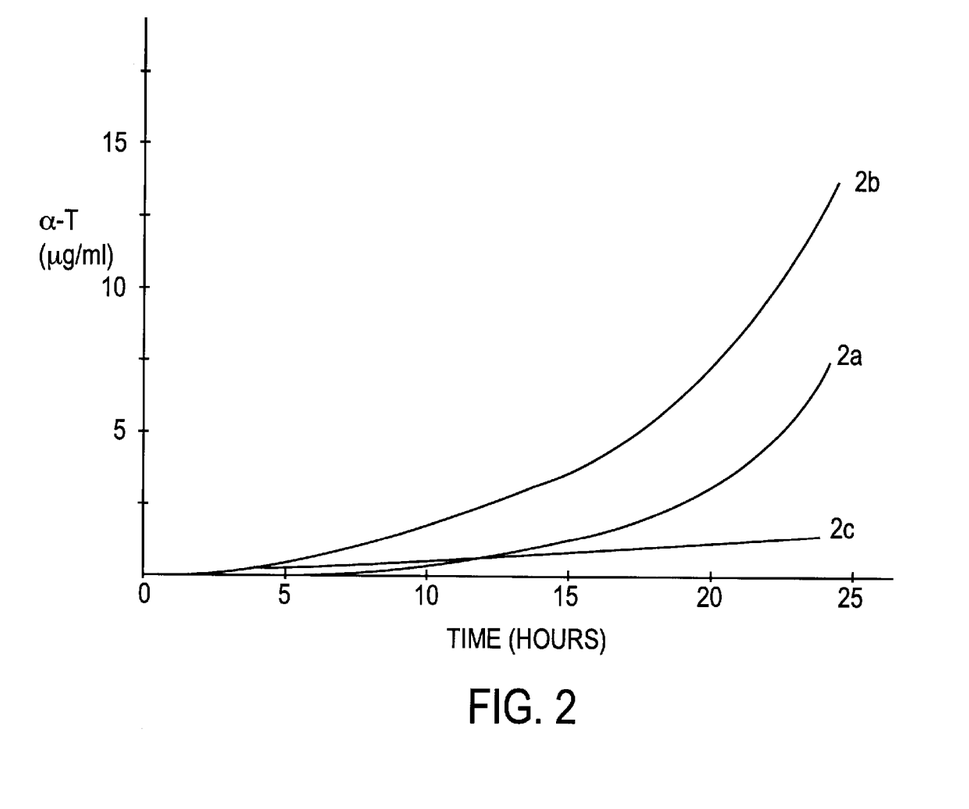
FIG. 2 shows the absorption and bioavailability of Vitamin E (*2a*) and α-tocopherol with medium chain triglycerides (*2b*), which enhance absorption and bioavailability, and starch (*2c*), which has slow absorption and bioavailability.

Oral LCP tablets similar to the tablets discussed in Example 8 were prepared, but in place of a portion of the phospholipid, 30% by weight of α-tocopherol was mixed with 70% powdered phospholipid in a food processor. After extrusion, the LCP was cut into lengths having a weight of 5 mg each. These were fed to Golden Syrian hamsters (Charles River Laboratories, Wilmington, Mass.). The hamsters were bled after dosage every five hours and their serum analyzed for tocopherol content. FIG. 2a shows the absorption and bioavailability of the Vitamin E up to 24 hours post dosage.

EXAMPLE 15

Oral LCP tablets similar to the tablets discussed in Example 8 were prepared, but in place of a portion of the phospholipid, 30% by weight of α-tocopherol and 2% by weight of Medium Chain Triglycerides were mixed with 68% powdered phospholipids in a food processor. After extrusion the LCP was cut into lengths having a weight of 5 mg each. These were fed to Golden Syrian hamsters. The hamsters were bled after dosage every five hours and their serum analyzed for α-tocopherol content. FIG. 2b shows the enhanced absorption and bioavailability of the α-tocopherol with the use of MCT as an adjunct.

EXAMPLE 16

A combination of 30% α-tocopherol and 70% starch was mixed in a food processor without phospholipids. This mixture was weighed into dosages of 5 mg each and fed to Golden Syrian hamsters. The hamsters were bled after dosage every five hours and their serum analyzed for α-tocopherol content. FIG. 2c proves the slow absorption and bioavailability of α-tocopherol into the blood.

EXAMPLE 17

A study was performed to compare the effects of cholesterol reduction using the 2% LCP alone, 0.01% Lescol (a HMG CoA reductase inhibitor) alone, and a combination of 0.01% Lescol mixed with the phospholipids and extruded to create the LCP. The dosage was administered to Golden Syrian hamsters which were bled after two weeks to determine the cholesterol lowering effects. Table 3 shows that the LCP and Lescol act additively to reduce the serum cholesterol levels.

TABLE 3

| Diet | Total Cholesterol | Non HDL | HDL |
|---|---|---|---|
| Control | 4.83 ± 1.45 | 2.69 ± 1.18 | 2.14 ± 0.38 |
| 2% LCP | 4.58 ± 0.77 | 2.29 ± 0.55 | 2.29 ± 0.21 |
| 0.01% Lescol | 3.37 ± 0.67 | 1.61 ± 0.63 | 1.77 ± 0.16 |
| 2% LCP + 0.01% Lescol | 3.13 ± 0.63 | 1.27 ± 0.20 | 1.86 ± 0.25 |

What is claimed is:

1. A pharmaceutical or cosmetic composition comprising lecithin, wherein said lecithin:
   (i) is a liquid crystal solid;
   (ii) has a homogenous and continuous structure;
   (iii) is transparent or translucent;
   (iv) has a bulk density of 0.95 to 1.2; and
   (v) is structurally deformable and shapeable into a dosage form suitable for oral or topical administration.

2. The composition of claim 1, comprising between 20% and 100% lecithin.

3. The composition of claim 2 comprising between 30% and 100% lecithin.

4. The composition of claim 3 comprising between 40% and 100% lecithin.

5. The composition of claim 4 comprising between 50% and 100% lecithin.

6. The composition of claim 5 comprising between 60% and 100% lecithin.

7. The composition of claim 6 comprising between 70% and 100% lecithin.

8. The composition of claim 7 comprising between 80% and 100% lecithin.

9. The composition of claim 1 which is of a size, shape and texture suitable for use as a cosmetic bar for moisturizing the skin.

10. The composition of claim 9, wherein said additives comprise fragrances, oils, moisturizers, vitamins, UV blockers, humectants, cleansers, colloidal meals, abrasives, herbal extracts, phytochemicals or combinations thereof.

11. The composition of claim 10, wherein said additive is between about 0.01% and about 80% by weight of said composition.

12. The composition of claim 1 further comprising a lipid-soluble nutrient and/or an active ingredient, wherein the amount of said nutrient or active ingredient is equal to between about 0.01 % and about 80% by weight of said composition.

13. The composition of claim 12 in the form of a tablet further comprising an intimate mixture of the lecithin and said lipid-soluble nutrient and/or active ingredient.

14. The composition of claim 12 in the shape of a capsule, wherein said capsule is comprised of said lecithin and said active ingredient.

15. The composition of claim 12, wherein said active ingredient is an isoflavone.

16. A high density lecithin product formed by the process comprising compressing and/or extruding a composition comprising between about 20% and 100% by weight de-oiled lecithin and having an acetone insoluble content equal to at least about 90%, for at least 15 seconds at a pressure of at least 100 psig so as to increase the density of said de-oiled lecithin to form said lecithin product having a density ranging between about 0.95 and 1.2.

* * * * *